US009918662B2

(12) United States Patent
Breitner

(10) Patent No.: US 9,918,662 B2
(45) Date of Patent: Mar. 20, 2018

(54) MEASURING CERVICAL SPINE POSTURE USING NOSTRIL TRACKING

(71) Applicant: Victoria Anna Breitner, Oshawa (CA)

(72) Inventor: Victoria Anna Breitner, Oshawa (CA)

(*) Notice: Subject to any disclaimer, the term of this patent is extended or adjusted under 35 U.S.C. 154(b) by 297 days.

(21) Appl. No.: 14/929,471

(22) Filed: Nov. 2, 2015

(65) Prior Publication Data

US 2017/0014052 A1  Jan. 19, 2017

Related U.S. Application Data

(60) Provisional application No. 62/191,574, filed on Jul. 13, 2015.

(51) Int. Cl.
*A61B 5/00* (2006.01)
*A61B 5/11* (2006.01)
*A61B 5/107* (2006.01)
*G06K 9/00* (2006.01)

(52) U.S. Cl.
CPC .......... *A61B 5/1116* (2013.01); *A61B 5/0077* (2013.01); *A61B 5/1071* (2013.01); *A61B 5/1079* (2013.01); *A61B 5/1128* (2013.01); *A61B 5/486* (2013.01); *A61B 5/6898* (2013.01); *A61B 5/725* (2013.01); *A61B 5/7246* (2013.01); *A61B 5/7267* (2013.01); *A61B 5/7278* (2013.01); *A61B 5/742* (2013.01); *A61B 5/746* (2013.01); *G06K 9/00* (2013.01)

(58) Field of Classification Search
CPC ....... A61B 5/11; A61B 5/1116; A61B 5/0077; A61B 5/1071; A61B 5/1079; A61B 5/1128; A61B 5/6898; A61B 5/7278; A61B 5/7246; A61B 5/746; A61B 5/486
See application file for complete search history.

(56) References Cited

U.S. PATENT DOCUMENTS

| 8,121,370 | B2* | 2/2012 | Dewaele | ............... G06T 3/0068 |
| | | | | 345/629 |
| 9,082,235 | B2* | 7/2015 | Lau | .......................... G07C 9/00 |
| 9,183,429 | B2* | 11/2015 | Qi | ....................... G06K 9/00221 |
| 9,262,671 | B2* | 2/2016 | Unzueta | ............. G06K 9/00281 |
| 9,516,259 | B2* | 12/2016 | Zheng | ....................... H04N 5/76 |
| 9,517,029 | B2* | 12/2016 | Gomi | .................... A61B 5/0077 |
| 9,750,414 | B2* | 9/2017 | Lane | ........................ A61B 5/01 |
| 9,770,213 | B2* | 9/2017 | Kirenko | ............. A61B 5/02416 |

* cited by examiner

*Primary Examiner* — Max Hindenburg
(74) *Attorney, Agent, or Firm* — Edgar Chana Law

(57) ABSTRACT

A method for detecting deviation from a preferred cervical spine posture when using a mobile device is disclosed. The mobile device uses a front-facing camera to capture images of the user and apply a nostril tracking algorithm to the images. The nostril tracking algorithm is used in real-time to measure displacement of the user's nostrils and correlate the nostril displacement to a cervical spine flexion angle. The user's cervical spine flexion angle is communicated using an alarm device, such as a row of lights, which allows the user to monitor and correct their posture and avoid potential injury.

20 Claims, 4 Drawing Sheets

MEASURING CERVICAL SPINE POSTURE USING NOSTRIL TRACKING

CROSS-REFERENCE TO RELATED APPLICATIONS

This application claims the benefit of U.S. Provisional Application No. 62/191,574, filed Jul. 13, 2015.

FIELD

The present disclosure relates generally to a computing devices used to improve posture. More particularly, the disclosure relates to using a front-facing camera of a mobile device to monitor cervical spine posture.

BACKGROUND

The use of computing devices, including desktop computer, laptops, tablets, and mobile phones, has increased dramatically over the last few decades. Many occupations require some form of computer work and sometimes the same individual will continue to use a computing device at home for leisure. Without proper ergonomic assessments or interventions, the users of these computing devices may be subjecting themselves to poor posture and potential musculoskeletal injuries.

There has been substantial research and guidelines surrounding the use of traditional desktop computers but much of this research does not apply to mobile computing devices. Much of the current research investigating computer and mobile device usage have used sitting postures, short task durations including breaks, and have not observed the frequency of postural changes. This research is not representative of the frequency and duration of mobile device usage from modern day users.

Recent research has discovered that prolonged use of mobile devices can lead to poor posture, particularly a forward-tilted head posture that puts increased stress on cervical vertebrae. This poor posture can be caused by users hunching over and flexing their neck forward when using their mobile device for prolonged periods. The weight seen by the spine dramatically increases when flexing the head forward at varying degrees. Loss of the natural curve of the cervical spine leads to incrementally increased stresses about the cervical spine. These stresses may lead to early wear, tear, degeneration, and possibly surgeries. Mobile devices are also more frequently used by teenagers and youths who are still developing their musculoskeletal system. Forward-tilted head posture has also been shown to promote changes in heart rate and breathing.

There have been several human head and face tracking solutions for monitoring or improving posture when using a mobile device. All of these solutions have various problems. Some of them cannot work in real-time, others are not robust enough. Some methods even need special equipment in their application, such as an IR camera to locate and track pupils by highlighting them in images.

Liu, J., Liu, C. & Zhao, Z. (2012). "Head gesture recognition based on LK algorithm and GentleBost". *Advances in Information Sciences and Service Sciences*, (4), 4, 158-167 (hereinafter referred to as Liu et al.) describes the use of nostril tracking to monitor human head movements such as nodding, shaking, bowing, etc. Nostril tracking is found to be robust as nostril shape does not change with age, race or gender.

SUMMARY

According to a first aspect, a method is for detecting deviation from a preferred cervical spine posture when using a mobile device. The method comprises obtaining a calibration image from a front-facing camera of the mobile device; locating nostrils in the calibration image; obtaining a plurality of tracking images obtained from the front-facing camera of the mobile device and locating the nostrils in the tracking images; measuring a nostril displacement of the nostrils between the tracking images and the calibration image; correlating the nostril displacement to a cervical spine flexion angle; and comparing the cervical spine flexion angle to an acceptable range of cervical spine flexion.

In some aspects, the method can also associate the difference between cervical spine flexion angle and the acceptable range of cervical spine flexion to an alarm severity and indicate the alarm severity using an alarm device coupled to the mobile device. The alarm severity can be increased according to a length of time that the cervical spine flexion angle is outside the acceptable range of cervical spine flexion. Obtaining the calibration image can also include providing instructions for the user to position their head and neck in a neutral position. The method can use a Lucas-Kanade method using a least squares criterion to measure the nostril displacement between tracking images.

In some aspects, locating the nostrils can include performing facial detection to define a face on any one of the calibration image or at least one of the tracking images; and obtaining a nostril region portion of the image. The nostril region portion of the image can be $2/7$ to $5/7$ of the face width and $1/2$ to $3/4$ the face height. In a further aspect, locating the nostrils can include identifying one or more nostril candidates in the image, the nostril candidate having a small pixel window relative to the image size; applying an edge detection algorithm on the nostril candidates to obtain a nostril candidate matrix for each nostril candidate; and comparing each nostril candidate matrix to a nostril classifier matrix to identify the nostril. The edge detection algorithm can use a Gabor filter. The nostril candidate matrix can be obtained by varying the Gabor filter coefficients, filter orientation, and spatial frequency of the Gabor filter. The nostril region portion of the image can be gray-scaled to assist with edge detection.

In still other aspects, the nostril classifier matrix can be obtained using a machine learning boosting algorithm trained against a representative sample of positive nostril candidates and negative nostril candidates. The machine learning boosting algorithm can be Gentle Boost algorithm variant. Comparison of the nostril candidate matrices with the nostril classifier matrix can seek to minimize the weighted error with the nostril classifier matrix.

According to a second aspect, a mobile device is disclosed comprising a forward facing camera; a display; a memory for storing instructions; and one or more processors configured to execute the instructions to: obtain a calibration image from the front-facing camera; locate nostrils in the calibration image; obtain a plurality of tracking images obtained from the front-facing camera and locate the nostrils in the tracking images; measure a nostril displacement of the nostrils between the tracking images and the calibration image; correlate the nostril displacement to a cervical spine flexion angle; and compare the cervical spine flexion angle to an acceptable range of cervical spine flexion.

In some aspects, the mobile device can further include an alarm device, and the one or more processors can be further configured to associate the difference between cervical spine flexion angle and the acceptable range of cervical spine flexion to an alarm severity; and indicate the alarm severity to the alarm device. The alarm device can be a row of lights or it can be integrated with the mobile device display. It can also provide a progressive scale to indicate severity of deviation from the preferred posture.

In some aspects, the processors can be further configured to identify one or more nostril candidates in the image, the nostril candidate having a small pixel window relative to the image size; apply an edge detection algorithm on the nostril candidates to obtain a nostril candidate matrix for each nostril candidate; and compare each nostril candidate matrix to a nostril classifier matrix to identify the nostril.

BRIEF DESCRIPTION OF THE DRAWINGS

For a better understanding of the various embodiments described herein and to show more clearly how they may be carried into effect, reference will now be made, by way of example only, to the accompanying drawings which show at least one exemplary embodiment, and in which.

DESCRIPTION OF VARIOUS EMBODIMENTS

It will be appreciated that for simplicity and clarity of illustration, where considered appropriate, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing some possible implementations of various embodiments.

The embodiments of the systems, devices and methods described herein may be implemented in hardware or software, or a combination of both. Some of the embodiments described herein may be implemented in computer programs executing on programmable computers, each computer comprising at least one processor, a computer memory (including volatile and non-volatile memory), at least one input device, and at least one output device. For example, and without limitation, the programmable computers may have multiple processors and at least one network interface device. Program code may operate on input data to perform the functions described herein and generate output data.

Figure 1:
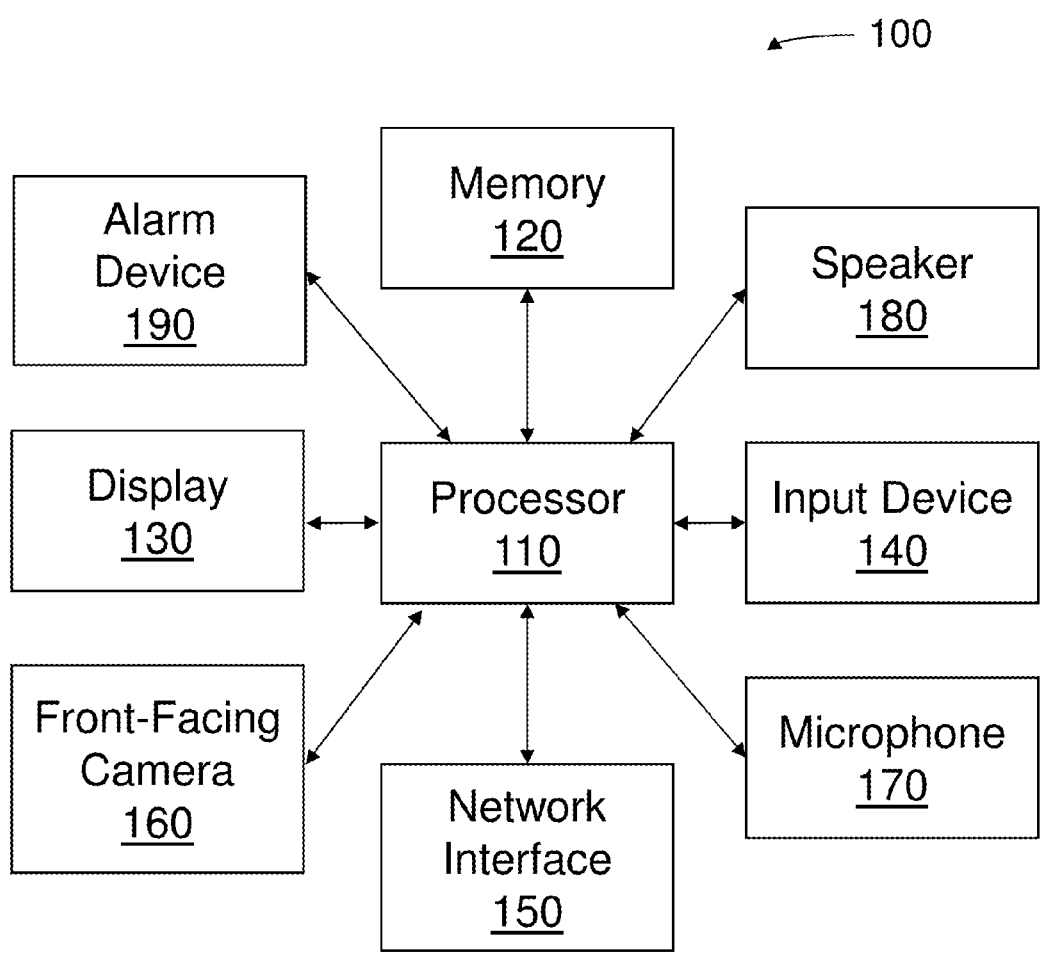
FIG. 1 is a block diagram of a mobile device having a front-facing camera.

Reference is first made to FIG. 1, shown is a block diagram of a mobile device 100 that can include a processor 110, memory 120, display 130, and input device 140. A network interface 150 can be provided to allow mobile device 100 to communicate with other computing devices over a communication network. Mobile device 100 can further include a front-facing camera 160, a microphone 170, and a speaker 180. Front-facing camera 160 is a camera that is positioned to capture an image of the user of mobile device 100. Front-facing camera 160 has a sufficient resolution to capture and measure nostril displacement, and is preferably capable of capturing images at high-definition resolutions. Examples of mobile device 100 can include mobile computing devices, such as mobile phones, laptop computers or tablet computing devices.

An alarm device 190 can be included on mobile device 100 to alert a user to improper posture. Alarm device 190 can be a progressive alarm that indicates the severity of the deviation from a preferred posture. For example, alarm device 190 can include a row of lights (e.g. a row of light emitting diodes across the top of the display) with each light representing an increasing severity of posture deviation from left to right. Some embodiments could also use a color scale to represent severity, for example, by using green, amber and red lights. Other embodiments could use a row of lights to indicate proper posture, for example, the more lights that are maintained, then the more correct the cervical posture and less harmful to the user so that the user is encouraged to maintain all of the lights to have a proper posture.

In some embodiments, alarm device 190 can be implemented in software and integrated with display 130 such that a portion of the display 130 is used to indicate the severity of posture deviation. For example, a top portion of the display can be used to display a row of lights, a bar, or a changing color light that indicate severity of posture deviation. Other embodiments of mobile device 100 can also use alarm device 190 to control settings (such as brightness, contrast, color settings, etc.) of display 130 such that display 130. For example, if a significant posture deviation is detected then alarm device 190 can change the settings of display 130, for example by dimming the brightness of the display, until the user corrects their posture.

Figure 2:
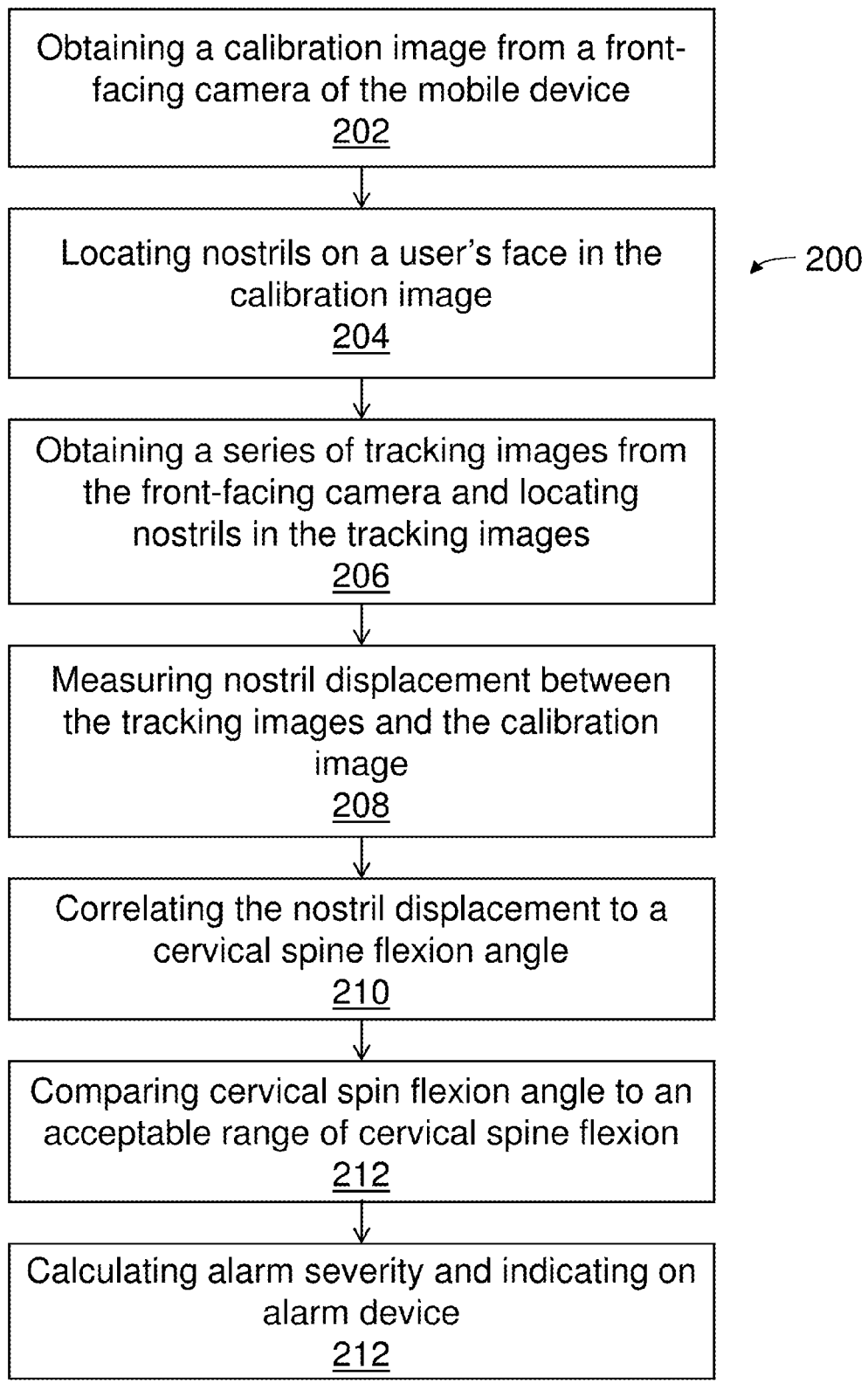
FIG. 2. is a flowchart diagram of a method for detecting deviation from a preferred cervical spine posture when using the mobile device of FIG. 1.

Referring now to FIG. 2, shown is a method 200 for detecting a deviation from a preferred cervical spine posture. Method 200 can be implemented by program instructions stored in memory 120 and executed by processor 110 of mobile device 100. Method 200 uses a nostril detection and displacement algorithm to measure deviation from a neutral cervical spine position quickly and to provide feedback to using alarm device 190.

At step 202 a calibration image is obtained from a front-facing camera 160 of mobile device 100. Step 202 can be initiated by a user input to begin the calibration process. A demonstrational video or diagrams can be shown on display 130 to illustrate a preferred neutral spine position. The preferred cervical spine posture is a neutral position with the individuals ear lobes aligned above the shoulders. In some embodiments, step 202 can further include capturing calibration images with the head and neck in various positions in order to provide other reference points for measuring nostril displacement.

The calibration process can further include ambient light detection and use of a flash associated with the camera to obtain suitable images. Preferably, the user is instructed to operate in an environment with adequate lighting. Some embodiments could also employ infrared imaging using an additional sensor to assist with darker environments.

Next at step 204, nostrils on the user's face are located within the calibration images. Nostril location can be performed using an image recognition algorithm such as that detailed in FIG. 3. Foreground extraction can also be involved in the calibration process to assist with locating nostrils in the image. Calibration will be successful if nostrils are located in the calibration image and success can be indicated on alarm device 190, for example, by lighting up the entire row of lights or a status bar on display 130. If calibration is unsuccessful, the user will be directed to repeat step 202 and correct the error (e.g. poor lighting, face outside of frame, etc.).

After calibration steps, a series of tracking images are continually captured by front-facing camera 160 and the nostrils of the user are located in the tracking images in step 206. Head movement is a continuous and must be measured over a series of tracking images. Multiple tracking images are also required to discard spurious head movements that may be unrelated to posture (e.g. turning away from the camera, nodding, etc.).

Tracking images can be captured using real-time video (e.g. at a high capture rate, such as 60 images per second) or at a more delayed rate (e.g. three images per second). The nostril tracking and displacement measuring algorithms described herein, such as those described with respect to FIG. 3, allow for capturing and processing tracking images at a high rate. In some embodiments the capture rate can vary in order to conserve battery power. An exponential back-off algorithm can be used to vary the capture rate when there is no posture deviation detected.

Next, at step 208, the nostril displacement is measured between the captured tracking images and the calibration images. Computer vision algorithms can be used measure displacement. Preferably, the Lucas-Kanade method (or LK method), or a variant thereof, is used that relies on the optical flow between images to be essentially constant in a local neighborhood of the feature under consideration, and solves the basic optical flow equations for all pixels in that neighborhood using the least squares criterion. This method allows the displacement between tracking images (or a series of tracking images) to be calculated quickly.

Other head movements can be discarded from consideration due to their temporal qualities. For example, brief head nods, shakes, bows, turning to face left or turning to face right should not cause variations in the alarm severity or be associated with a poor cervical spine position.

The measured nostril displacement is then correlated to a cervical spine flexion angle at step 210. For example, a ten pixel displacement downwards in a tracking image from the calibration image can correspond to a 5 degree cervical spine flexion angle. Calibration step 202 can also capture an additional calibration image with having a certain known cervical spine flexion angle, for example, by capturing an image with the user putting their chin on their chest which is equivalent to a 90 degree cervical spine flexion angle. Measuring displacement step 208 and correlation step 210 can compare displacement between multiple calibration images having known cervical spine angles to determine a cervical spine flexion angle.

The cervical spine flexion angle determined in step 210 is next compared to an acceptable range of cervical spine flexion at step 212. The best posture range is between neutral and 10 degrees of cervical spine flexion, but a range between 15 and 25 degrees of cervical spine flexion would also be considered acceptable. A poor cervical posture can be any cervical spine flexion angle that exceeds 30 degrees.

At step 212, the greater the difference in cervical spine flexion angle from the acceptable range of cervical spine flexion can be associated with an alarm severity. This alarm severity can then be indicated by alarm device 190 so that the user of mobile device 100 is aware of any poor posture and can correct their posture. Preferably, alarm device 190 is a progressive alarm device to indicate severity.

Alarm severity calculation in step 212 can also incorporate temporal factors. For example, if a non-ideal cervical posture is held for a too long of a time then alarm severity can be increased to encourage the user to move from a static posture. Alarm severity can also be increased after any prolonged period to encourage the user to stretch or perform posture exercises. Also, temporary movements, such as a head nod, can be discarded from affecting alarm severity.

Figure 3:
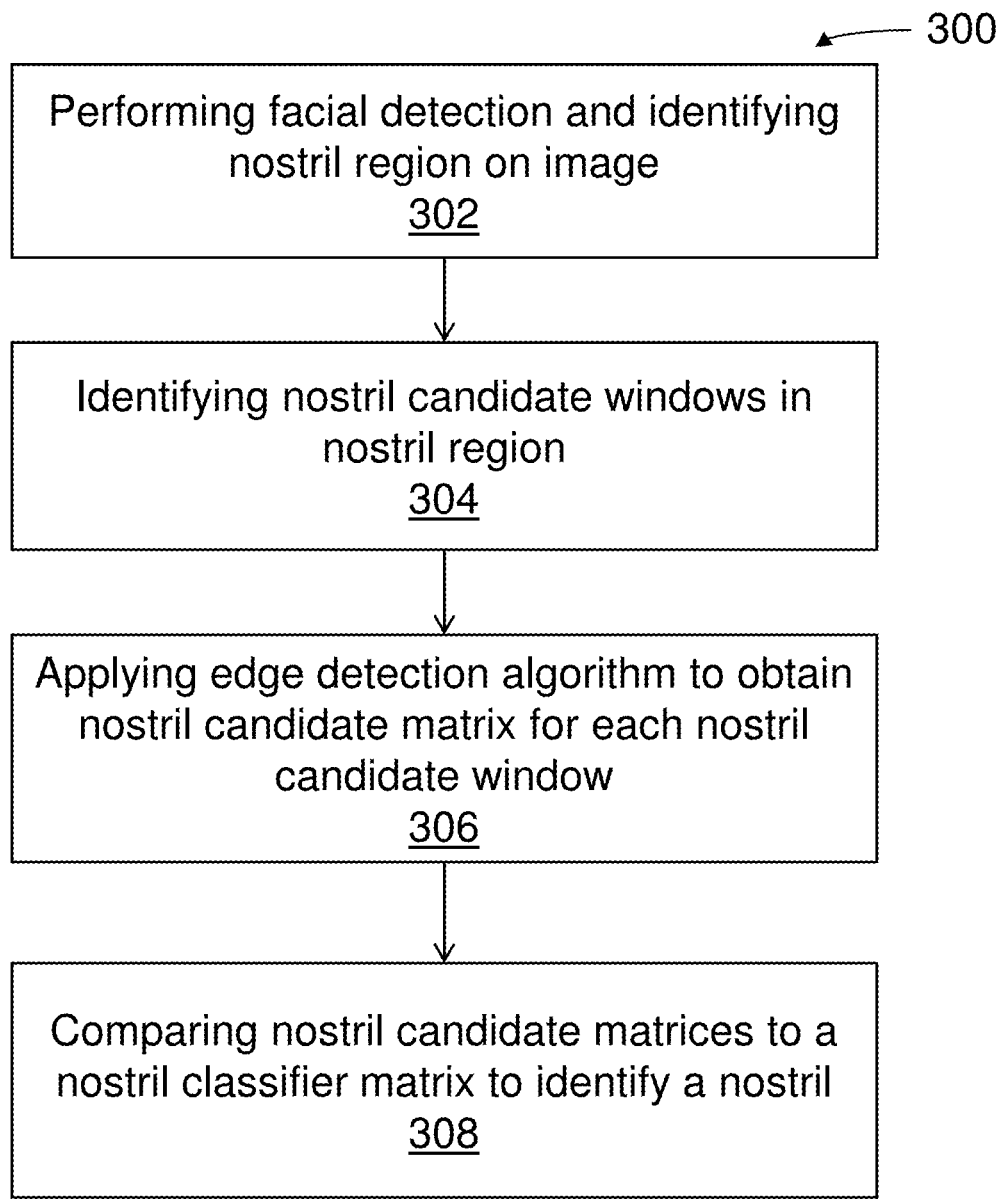
FIG. 3 is a flowchart diagram of a method for locating nostrils in an image that can be used in the method of FIG. 2.

Reference is now made to FIG. 3, a flowchart diagram of a nostril locating method 300 for locating nostrils in an image that can be used in the method 200 of FIG. 2. Nostril locating method 300 uses a machine learning algorithm to quickly ascertain whether a potential nostril candidate is in fact a human nostril. Nostril locating method 300 can be used on calibration images and tracking images.

First, at step 302, a facial detection algorithm is used to identify a face within an image captured by front-facing camera 160. Preferably, facial detection algorithm can operate quickly to define the bounds of a face within the image. Any known facial detection algorithm can be used with a preference for facial detection algorithms that can identify the facial boundary quickly. Using the facial detection outputs, a nostril region portion of the image is obtained.

Figure 4:
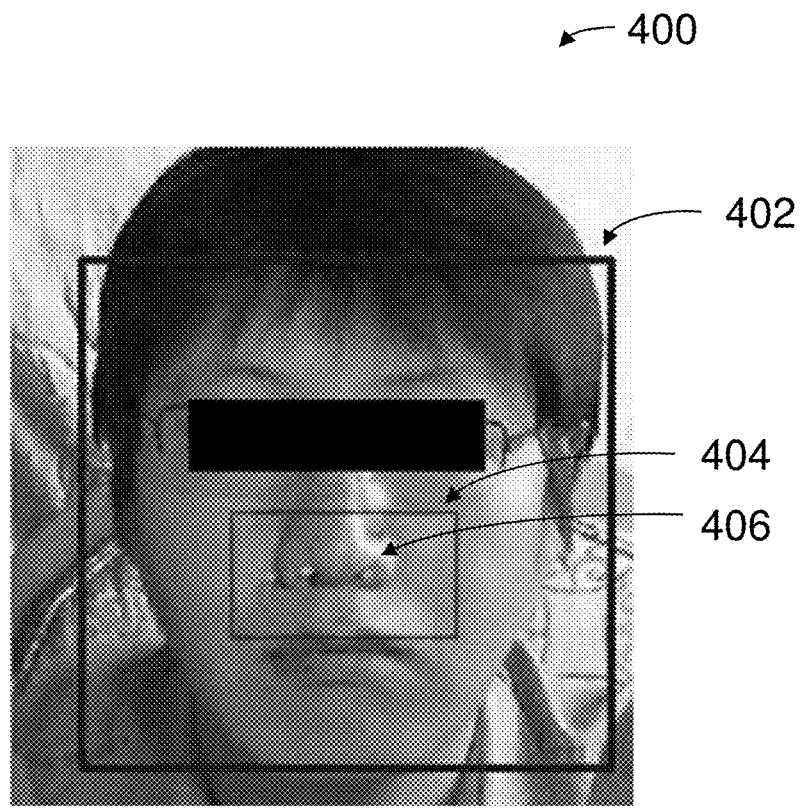
FIG. 4 is a photograph of an individual identifying a face detected region and a nostril region within the face detected region.

The nostril region portion of the image can be obtained using known facial dimensions. For example, using the facial boundary the nostril region portion of the between 2/7 to 5/7 of the face width and between 1/2 and 3/4 of the face height. The image in FIG. 4 illustrates an image 400 where the facial boundary 402 is identified and the nostril region portion 404 of image 400 is identified.

Returning to FIG. 3, at step 304 nostril candidates are identified within the nostril region portion 404. Image 400 illustrates a number of nostril candidates 406 that can potentially be a human nostril in image 400. Nostril candidates are focused on a smaller pixel window relative to the image size (e.g. 3×3 pixels, 5×5 pixels, 7×7 pixels).

Next, in step 306, an edge detection algorithm is applied to each nostril candidate window to obtain matrix for each nostril candidate window by varying the edge detection aspects. Preferably a Gabor filter is used as the edge detection algorithm and the matrix can be obtained by varying the Gabor filter coefficients, filter orientation, and the spatial frequency of the Gabor filter. It may also be preferable to gray-scale each nostril candidate window (or a relevant portion of the image) prior to applying edge detection algorithms in step 306.

For example, a feature vector can be extracted from a 13×13 pixel image nostril candidate window centered on a nostril candidate. The nostril candidate window can be filtered with a pool of 48 Gabor filters at 8 orientations and 6 spatial frequencies (2:12 pixels/cycle at 1/2 octave steps) to obtain a nostril candidate matrix of feature vectors representing that nostril candidate. Fewer Gabor filters, orientations or spatial frequencies can be used reduce processing requirements for more efficient and faster nostril identification.

The nostril candidate matrix can then be compared to a nostril classifier matrix to identify a nostril in step 308. Using a nostril classifier matrix allows for a computationally efficient and fast method of identifying nostrils in the image that can function in real-time on a processor in a mobile device. The comparison method can use a weighted least-squared error in comparing each of the nostril candidate matrices with the nostril classifier matrix that seeks to minimize the weighted error below a certain detection threshold.

The nostril classifier matrix can be obtained using a machine learning algorithm that is trained against a representative sample of positive nostril candidates (i.e. nostril candidate window contains a human nostril) and negative nostril candidates (i.e. nostril candidate window does NOT contain a human nostril). The machine learning algorithm can be a boosting algorithm, such as the GentleBoost algorithm. Learning examples can use a smaller image window (e.g. 5×5 pixel window) centered on the proposed nostril feature to obtain the nostril classifier matrix. The nostril classifier matrix can contain a number of positively and negatively weighted vectors obtained from the examples.

While the exemplary embodiments have been described herein, it is to be understood that the invention is not limited to the disclosed embodiments. The invention is intended to cover various modifications and equivalent arrangements included within the spirit and scope of the appended claims, and scope of the claims is to be accorded an interpretation that encompasses all such modifications and equivalent structures and functions.

The invention claimed is:

1. A method for detecting deviation from a preferred cervical spine posture when using a mobile device, the method comprising:
   obtaining a calibration image from a front-facing camera of the mobile device;
   locating nostrils in the calibration image;
   obtaining a plurality of tracking images obtained from the front-facing camera of the mobile device and locating the nostrils in the tracking images;
   measuring a nostril displacement of the nostrils between the tracking images and the calibration image;
   correlating the nostril displacement to a cervical spine flexion angle; and
   comparing the cervical spine flexion angle to an acceptable range of cervical spine flexion.

2. The method of claim 1 further comprising:
   associating the difference between cervical spine flexion angle and the acceptable range of cervical spine flexion to an alarm severity; and
   indicating the alarm severity using an alarm device.

3. The method of claim 2 further comprising:
   increasing alarm severity according to a length of time that the cervical spine flexion angle is outside the acceptable range of cervical spine flexion.

4. The method of claim 1 wherein obtaining the calibration image further comprises:
   providing instructions for the user to position their head and neck in a neutral position.

5. The method of claim 1 wherein measuring the nostril displacement between tracking images uses a Lucas-Kanade method using a least squares criterion.

6. The method of claim 1 wherein locating nostrils further comprises:
   performing facial detection to define a face on any one of the calibration image or at least one of the tracking images; and
   obtaining a nostril region portion of the image.

7. The method of claim 6 wherein the nostril region portion of the image is 2/7 to 5/7 of the face width and 1/2 to 3/4 the face height.

8. The method of claim 1 wherein locating nostrils further comprises:
   identifying one or more nostril candidates in the image, the nostril candidate having a small pixel window relative to the image size;
   applying an edge detection algorithm on the nostril candidates to obtain a nostril candidate matrix for each nostril candidate; and
   comparing each nostril candidate matrix to a nostril classifier matrix to identify the nostril.

9. The method of claim 8 wherein the edge detection algorithm is a Gabor filter.

10. The method of claim 9 wherein applying the edge detection algorithm to obtain the nostril candidate matrix comprises varying the Gabor filter coefficients, filter orientation, and spatial frequency of the Gabor filter.

11. The method of claim 8 further comprising grayscaling the one or more nostril candidates.

12. The method of claim 8 wherein the nostril classifier matrix is obtained using a machine learning boosting algorithm trained against a representative sample of positive nostril candidates and negative nostril candidates.

13. The method of claim 12 wherein the machine learning boosting algorithm is a Gentle Boost algorithm.

14. The method of claim 8 wherein comparing each nostril candidate matrix seeks to minimize the weighted error with the nostril classifier matrix.

15. A mobile device comprising:
   a forward facing camera;
   a display;
   a memory for storing instructions; and
   one or more processors configured to execute the instructions to:
      obtain a calibration image from the front-facing camera;
      locate nostrils in the calibration image;
      obtain a plurality of tracking images obtained from the front-facing camera and locate the nostrils in the tracking images;
      measure a nostril displacement of the nostrils between the tracking images and the calibration image;
      correlate the nostril displacement to a cervical spine flexion angle; and
      compare the cervical spine flexion angle to an acceptable range of cervical spine flexion.

16. The mobile device of claim 15 further comprising an alarm device, and the one or more processors are further configured to associate the difference between cervical spine flexion angle and the acceptable range of cervical spine flexion to an alarm severity; and indicate the alarm severity to the alarm device.

17. The mobile device of claim 16 wherein the alarm device is a row of lights.

18. The mobile device of claim 16 wherein the alarm device is a progressive scale to indicate the severity of deviation of the cervical spine flexion angle from the acceptable range of cervical spine flexion.

19. The mobile device of claim 16 wherein the alarm device is integrated with the display.

20. The mobile device of claim 15 wherein the one or more processors are further configured to:
   identify one or more nostril candidates in the image, the nostril candidate having a small pixel window relative to the image size;
   apply an edge detection algorithm on the nostril candidates to obtain a nostril candidate matrix for each nostril candidate; and
   compare each nostril candidate matrix to a nostril classifier matrix to identify the nostril.

* * * * *